(12) United States Patent　　(10) Patent No.: US 7,071,392 B2
McClure　　(45) Date of Patent: Jul. 4, 2006

(54) SOYBEAN CULTIVAR CL615261

(75) Inventor: Donald B. McClure, Melbourne (CA)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 11/084,510

(22) Filed: Mar. 18, 2005

(65) Prior Publication Data

US 2005/0268361 A1　Dec. 1, 2005

Related U.S. Application Data

(60) Provisional application No. 60/574,777, filed on May 27, 2004.

(51) Int. Cl.
*A01H 1/00*　(2006.01)
*A01H 4/00*　(2006.01)
*A01H 5/00*　(2006.01)
*A01H 5/10*　(2006.01)
*C12N 15/82*　(2006.01)

(52) U.S. Cl. ...................... 800/312; 800/260; 800/278; 800/279; 800/281; 800/284; 800/298; 800/300; 800/301; 800/302; 800/303; 435/415; 435/426

(58) Field of Classification Search ................ 800/312, 800/260, 278, 279, 281, 284, 298, 300, 301, 800/302, 303; 435/415, 426
See application file for complete search history.

(56) References Cited

U.S. PATENT DOCUMENTS 6,111,169 A * 8/2000 Sebern ....................... 800/312
6,350,938 B1 * 2/2002 Threlkeld et al. ........... 800/312

* cited by examiner

*Primary Examiner*—Russell P. Kallis
(74) *Attorney, Agent, or Firm*—Dana Rewoldt

(57) ABSTRACT

The present invention is a novel soybean cultivar designated CL615261 with high yield potential, tolerance to Roundup™ herbicide, mid Group I maturity, tolerance to Iron Deficiency Chlorosis and resistance to Phytophthora Root Rot, further including the plants and seeds of the cultivar CL615261, methods for producing a soybean plant by crossing the cultivar CL615261 with itself or another soybean plant. The invention also relates to soybean cultivar CL615261 further comprising one or more single gene traits, and to methods of producing a soybean having such traits by introgression, transformation or mutagenesis. The invention also includes using the soybean cultivar CL615261 to produce other soybean cultivars, breeding lines, and progeny.

21 Claims, No Drawings

SOYBEAN CULTIVAR CL615261

FIELD OF THE INVENTION

The present invention is in the field of soybean breeding, specifically to a new and distinctive soybean cultivar, designated CL615261.

BACKGROUND OF THE INVENTION

The present invention relates to a new and distinctive soybean cultivar, designated CL615261. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. These important traits may include higher seed yield, resistance to diseases and insects, better stems and roots, tolerance to drought and heat, and better agronomic quality.

Soybeans [*Glycine max* (L.) Merr.] are recognized to be naturally self-pollinated plants, while capable of undergoing cross-pollination, rarely do so in nature. However, soybeans can be bred by both self-pollination and cross-pollination techniques. Choice of breeding or selection methods depends on the mode of plant reproduction, the heritability of the trait(s) being improved, and the type of cultivar used commercially (e.g., F1 hybrid cultivar, pureline cultivar, etc.) For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.)

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climate and soil conditions, and further selections are then made during and at the end of the growing season. The development of new cultivars is unpredictable. This unpredictability is because the breeder's selection occurs in unique environments, with no control at the DNA level (using conventional breeding procedures,) and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. Thus, many cultivates that are developed do not contain a desired trait or set of traits and are dropped from further development. This inability to predict the genotype or phenotype of the final resulting cultivars results in the expenditure of large amounts of research monies to develop new soybean cultivars.

The development of new soybean cultivars requires the development and selection of soybean cultivars, the crossing of these cultivars and selection of superior hybrid crosses. The hybrid seed is produced by manual crosses between selected male-fertile parents or by using male sterility systems. These hybrids are selected for certain single gene traits such as pod color, flower color, pubescence color and/or herbicide resistance which indicate that the seed is truly a hybrid. Additional data on parental lines as well as the phenotype of the hybrid influence a breeder's decision whether to continue with the specific hybrid cross. Proper testing will detect the level of superiority or improvement over current cultivars.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents that possess favorable, complementary traits are crossed to produce an F1. An F2 population is produced by selfing one or several F1's. Selection of the best individuals may begin in the F2 population; then, beginning in the F3 the best individuals in the families are selected. Replicated testing of families can begin in the F4 generation to improve the effectiveness of selection for traits with low heritability. At an advanced stage of inbreeding (i.e., F6 and F7), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when the generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in several reference books (e.g., Allard R. W., Principles of Plant Breeding (Wiley & Sons, 1999); Simmonds N. W., Principles of Crop Improvement (Longman, 1979); Sneep J., Hendriksen A. J. T., Plant Breeding Perspectives (Centre for Agricultural Publishing, 1979.)

SUMMARY OF THE INVENTION

The present invention is a novel soybean cultivar designated CL615261 with high yield potential, tolerance to Roundup™ herbicide, mid Group I maturity, tolerance to Iron Deficiency Chlorosis and resistance to Phytophthora Root Rot. The invention relates to the seeds of cultivar CL615261, plants of the cultivar CL615261 and to methods of producing a soybean plant by crossing of the cultivar CL615261 by itself and another soybean genotype.

The invention is also directed to soybean cultivar CL615261 further comprising one or more genes, wherein the genes are transferred into soybean cultivar CL615261 using traditional non-transgenic breeding techniques or by using recombinant transgene technology. The invention further includes methods for producing a soybean plant by crossing the soybean cultivar CL615261, or the soybean cultivar further comprising one or more genes, with itself or with another soybean genotype.

The invention is further directed to methods for producing a soybean plant by crossing a first parent soybean plant with a second parent soybean plant, wherein the first or second soybean plant is the soybean plant from the soybean cultivar CL615261. Further, both first and second parent soybean plants may be from the soybean cultivar CL615261. Therefore, any methods using the soybean cultivar CL615261 are part of this invention: selfing, backcrosses, hybrid breeding and crosses to populations. All plants produced using soybean cultivar CL615261 as a parent are within the scope of the invention.

In another aspect of the invention, the one or more genes that are transferred into soybean cultivar CL615261 confer traits such as herbicide resistance, insect resistance, disease resistance, and nematode resistance or virus resistance. An additional trait relates to the production of thioredoxin and thioredoxin reductase enzymes for modifying grain digestibility and nutrient availability.

DETAILED DESCRIPTION OF THE INVENTION

A soybean cultivar needs to be highly homogeneous, homozygous and reproducible to be useful as a commercial cultivar. There are many analytical methods available to determine the homozygotic and phenotypic stability of these cultivars.

The oldest and most traditional method of analysis is the observation of phenotypic traits. The data is usually collected in field experiments over the life of the soybean plants to be examined. Phenotypic characteristics most often observed are for traits associated with seed yield, lodging resistance, disease resistance, emergence, maturity, plant height, shattering, flower color, pubescence color, pod color and hilum color.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The cultivar of the invention has shown uniformity and stability for all traits, as described in the following cultivar description information. It has been self-pollinated a sufficient number of generations, with careful attention to uniformity of plant type to ensure homozygosity and phenotypic stability. The line has been increased with continued observation for uniformity. No variant traits have been observed or are expected in CL615261. Soybean cultivar CL615261, being substantially homozygous, can be reproduced by planting seeds of the line, growing the resulting soybean plants under self-pollinating or sib-pollinating conditions, and harvesting the resulting seed, using techniques familiar to the agricultural arts.

Publications useful as references in interpreting the breeding history and data presented below include: Caldwell, B. E. ed. 1973. "Soybeans: Improvement, Production, and Uses" Amer. Soc. Agron. Monograph No. 16; Buttery, B. R., and R. I. Buzzell 1968. "Peroxidase Activity in Seed of Soybean Varieties" Crop Sci. 8: 722–725; Hymowitz, T. 1973. "Electrophoretic analysis of SBTI-A2 in the USDA Soybean Germplasm Collection" Crop Sci., 13: 420–421; Payne R. C., and L. F. Morris, 1976. "Differentiation of Soybean Varieties by Seedling Pigmentation Patterns" J. Seed. Technol. 1: 1–19. The disclosures of which are each incorporated by reference in their entirety.

Pedigree and Breeding History: CL615261 was selected from an F6 plant from the cross C389624/LX6002F1. C389624 is a Syngenta proprietary line and LX6002 is an F1 from the cross Korada/S14-M7. Korada is a commercial cultivar marketed by Semences Prograin Inc., Quebec, Canada and S14-M7 is a commercial cultivar developed by Syngenta Seeds, Inc.

The F1 and F2 generations were grown in Hawaii during the fall/winter of 1996–1997. The F3 generation was grown in Ontario, Canada during the summer of 1997. The F4 and F5 generations were grown in Hawaii. The F6 generation was grown in Ontario, Canada and 36 single plants were selected during the fall of 1998. The F1 –F6 generations were sprayed with Roundup™ herbicide to remove susceptible plants. The single plants were threshed individually and the progeny yield tested in a preliminary trial in 1999. One of these lines, CL615261, was selected on superior agronomic traits and advanced to wide area testing in 2000 and 2001 in Canada and the northern U.S.

CL615261 was also greenhouse screened in Arkansas for Phytopthora Root Rot resistance and found to possess the Rps1c gene conferring resistance to the disease.

Soybean cultivar CL615261 has the following morphological and other characteristics:

Descriptive Information:

| Plant Type: | Slender Bush |
|---|---|
| Hypocotyl Length: | Intermediate |
| Stem Termination: | Indeterminae |
| Pubescence Colour: | Tawny |
| Flower Colour: | Purple |
| Pod Colour: | Tan |
| Hilum Colour: | Imperfect yellow |
| Hypocotyl Colour: | Purple |
| Seed Coat Colour: | Yellow |
| Seed Peroxidase Activity: | High |
| Maturity Group: | 1 |
| Relative Maturity: | 1.5 |
| Ave. Seeds/Pound: | 2500 |
| Phytophthora Gene: | Rps1c |

The invention is further directed to methods for producing a soybean plant by crossing a first parent soybean plant with a second parent soybean plant, wherein the first or second soybean plant is the soybean plant from the soybean cultivar CL615261. Further, both first and second parent soybean plants may be from the soybean cultivar CL615261. Therefore, any methods using the soybean cultivar CL615261 are part of this invention: selfing, backcrosses, hybrid breeding and crosses to populations. All plants produced using soybean cultivar CL615261 as a parent are within the scope of the invention.

The invention also encompasses plants of cultivar CL615261, or a part thereof, further comprising one or more specific, single gene transferred traits. Such genes are introgressed into cultivar CL615261 from another soybean cultivar or are transformed into cultivar CL615261 using techniques and materials known to those persons skilled in the art. The introgression of the trait(s) into cultivar CL615261 is, for example, achieved by recurrent selection breeding, for example by backcrossing. The goal of a backcross protocol is to alter or substitute a single trait or characteristic in the original inbred. In one embodiment of the present invention, cultivar CL615261 (the recurrent parent) is first crossed to a donor inbred (the non-recurrent parent) that carries the appropriate gene(s) for the trait(s) in question. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes, i.e., will be like the recurrent parent for essentially all of the recurrent parent's physiological and morphological characteristics. (see, for example, Poehlman & Sleper (1995) Breeding Field Crops, 4th Ed., 172–175; Fehr (1987) Principles of Cultivar Development, Vol. 1: Theory and Technique, 360–376.)

The laboratory-based techniques described above, in particular RFLP and SSR, can be used in such backcrosses to identify the progenies having the highest degree of genetic identity with the recurrent parent. This permits one to accelerate the production of soybean cultivars having at least 90%, preferably at least 95%, more preferably at least 99% genetic identity with the recurrent parent, yet more preferably genetically identical to the recurrent parent, and further comprising the trait(s) introgressed from the donor patent. Such determination of genetic identity can be based on molecular markers used in the laboratory-based techniques described above.

The last backcross generation is then selfed to give pure breeding progeny for the gene(s) being transferred. The resulting plants have essentially all of the morphological and physiological characteristics of cultivar CL615261, in addition to the single gene trait(s) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

The cultivar of the invention can also be used for transformation where exogenous genes are introduced and expressed by the cultivar of the invention. Genetic variants created either through traditional breeding methods using cultivar CL615261 or through transformation of cultivar CL615261 by any of a number of protocols known to those of skill in the art are intended to be within the scope of this invention (see e.g. Trick et al. (1997) Recent Advances in Soybean Transformation, Plant Tissue Culture and Biotechnology, 3:9–26). In general, a transgene typically comprises a nucleotide sequence whose expression is responsible or contributes to the trait, under the control of a promoter capable of directing the expression of the nucleotide sequence at the desired time in the desired tissue or part of the plant. Constitutive promoters, tissue-specific promoters, inducible promoters, or other promoters known to those persons skilled in the art are used. The transgene may also comprise other regulatory elements such as for example translation enhancers or termination signals. In one embodiment of the present invention, the transgene nucleotide sequence transformed into cultivar CL615261 may include a coding sequence that is transcribed and translated into a protein. In another embodiment of the invention, the nucleotide sequence encodes an antisense RNA or a sense RNA that is not translated or only partially translated.

Production of a genetically modified plant tissue by transformation combines teachings of the present disclosure with a variety of techniques and expedients known in the art. In most instances alternate expedients exist for each stage of the overall process. The choice of expedients depends on the variables such as the plasmid vector system chosen for the cloning and introduction of the desired recombinant DNA molecule, as well as the particular structural gene, promoter elements and upstream elements used. Persons skilled in the art are able to select and use appropriate alternatives to achieve optimum functionality. Culture conditions for expressing desired structural genes and cultured cells are known in the art. Also as known in the art, soybeans are transformable and regenerable such that whole plants containing and expressing desired genes under regulatory control may be obtained. General descriptions of plant expression vectors and reporter genes and transformation protocols can be found in Gruber et al., "Vectors for Plant Transformation, in Methods in Plant Molecular Biology & Biotechnology" in Glich et al. (Eds. pp. 89–119, CRC Press, 1993.) Moreover GUS expression vectors and GUS gene cassettes are available from Clone Tech Laboratories, Inc., Palo Alto, Calif., while luciferase expression vectors and luciferase gene cassettes are available from Pro Mega Corp. (Madison, Wis.) General methods of culturing plant tissues are described by Maki et al. "Procedures for Introducing Foreign DNA into Plants" in Methods in Plant Molecular Biology & Biotechnology, Glich et al. (Eds. pp. 67–88 CRC Press, 1993); and by Phillips et al. "Cell-Tissue Culture and In-Vitro Manipulation" in Soybean & Soybean Improvement, 3rd Edition Sprague et al. (Eds. pp. 345–387) American Society of Agronomy Inc. et al. 1988.

Methods of introducing desired recombinant DNA molecule into plant tissue include the direct infection or co-cultivation of plant cells with *Agrobacterium tumefaciens*, Horsch et al., Science, 227:1229 (1985.) Descriptions of *Agrobacterium* vector systems and methods for *Agrobacterium*-mediated gene transfer provided by Gruber, et al. supra. Other useful methods include but are not limited to expression vectors introduced into plant tissues using a direct gene transfer method such as microprojectile-mediated delivery, DNA injection, electroporation and the like. More preferably expression vectors are introduced into plant tissues using the biolistic microprojectile delivery or *Agrobacterium*-medicated transformation. Transformed plants obtained via protoplast transformation are also intended to be within the scope of this invention.

Many traits have been identified that are not regularly selected for in the development of a new cultivar but that can be improved e.g. by backcrossing techniques or by genetic transformation. Using materials and methods well known to those persons skilled in the art, traits that are capable of being transferred to cultivar CL615261 include, but are not limited to, herbicide tolerance, resistance for bacterial, fungal, or viral disease, nematode resistance, insect resistance, enhanced nutritional quality, such as oil, starch and protein content or quality, improved performance in an industrial process, altered reproductive capability such as male sterility or male fertility, yield stability and yield enhancement. Other traits include the production of commercially valuable enzymes or metabolites.

Where more than one trait are introgressed into cultivar CL615261, it is preferred that the specific genes are all located at the same genomic locus in the donor, non-recurrent parent, preferably, in the case of transgenes, as part of a single DNA construct integrated into the donor's genome. Alternatively, if the genes are located at different genomic loci in the donor, non-recurrent parent, backcrossing allows to recover essentially all of the morphological and physiological characteristics of cultivar CL615261 in addition to the multiple genes in the resulting soybean cultivar.

The genes responsible for a specific, single gene trait are generally inherited through the nucleus. Known exceptions are, e.g. the genes for male sterility, some of which are inherited cytoplasmically, but still act as single gene traits. In a preferred embodiment, a transgene to be introgressed into cultivar CL615261 is integrated into the nuclear genome of the donor, non-recurrent parent or the transgene is directly transformed into the nuclear genome of cultivar CL615261. In another embodiment of the invention, a transgene to be introgressed into cultivar CL615261 is integrated into the plastid genome of the donor, non-recurrent parent or the transgene is directly transformed into the plastid genome of cultivar CL615261. In a further embodiment of the invention, a plastid transgene comprises one gene transcribed from a single promoter or two or more genes transcribed from a single promoter.

A non-exclusive list of traits or nucleotide sequences capable of being transferred into cultivar CL615261, using material and methods well known to those persons skilled in the art are as follows: genetic factor(s) responsible for resistance to brown stem rot (U.S. Pat. No. 5,689,035) or resistance to cyst nematodes (U.S. Pat. No. 5,491,081); a transgene encoding an insecticidal protein, such as, for example, a crystal protein of *Bacillus thuringiensis* or a vegetative insecticidal protein from *Bacillus cereus*, such as VIP3 (see, for example, Estruch et al. Nat Biotechnol (1997) 15:137–41; a herbicide tolerance transgene whose expression renders plants tolerant to the herbicide, for example, expression of an altered acetohydroxyacid synthase (AHAS) enzyme confers upon plants tolerance to various imidazolinone or sulfonamide herbicides (U.S. Pat. No. 4,761,373.) Other traits capable of being transformed into cultivar CL615261 include, for example, a non-transgenic trait conferring to cultivar CL615261 tolerance to imidazolinones or sulfonylurea herbicides; a transgene encoding a mutant acetolactate synthase (ALS) that renders plants resistant to inhibition by sulfonylurea herbicides (U.S. Pat. No. 5,013,659); a gene encoding a mutant glutamine synthetase (GS) resistant to inhibition by herbicides that are known to inhibit GS, e.g. phosphinothricin and methionine sulfoximine (U.S. Pat. No. 4,975,374); and a Streptomyces bar gene encoding a phosphinothricin acetyl transferase resulting in tolerance to the herbicide phosphinothricin or glufosinate (U.S. Pat. No. 5,489,520.) Other genes capable of being transferred into the cultivar CL615261 of the invention include toleration to inhibition by cyclohexanedione and aryloxyphenoxypropanoic acid herbicides (U.S. Pat. No. 5,162,602), which is conferred by an altered acetyl coenzyme A carboxylase (ACCase); transgenic glyphosate tolerant plants, which tolerance is conferred by an altered 5-enolpyruvyl-3-phosphoshikimate (EPSP) synthase gene; tolerance to a protoporphyrinogen oxidase inhibitor, which is achieved by expression of a tolerant protoporphyrinogen oxidase enzyme in plants (U.S. Pat. No. 5,767,373.) In yet another embodiment of the present invention, a transgene transformed or introgressed into cultivar CL615261 comprises a gene conferring tolerance to a herbicide and at least another nucleotide sequence for another trait, such as for example, insect resistance or tolerance to another herbicide. Another gene capable of being transferred into the cultivar CL615261 of the invention expresses thioredoxin and thioredoxin reductase enzymes for modifying grain digestibility and nutrient availability (U.S. Pat. Appl. No. 20030145347.)

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant that does not have the desired herbicide tolerance characteristic, and only those plants that have the herbicide tolerance gene are used in the subsequent backcross. This process is then repeated for the additional backcross generations.

Further reproduction of the cultivar can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333–337 (1991); Stephens, P. A. et al., "Agronomic Evaluation of Tissue-Culture-Derived Soybean Plants," Theor. Appl. Genet. (1991) 82:633–635; Komatsuda, T. et al., "Maturation and Germination of Somatic Embryos as Affected by Sucrose and Plant Growth Regulators in Soybeans Glycine gracilis Skvortz and Glycine max (L.) Merr.," Plant Cell, Tissue and Organ Culture, 28:103–113 (1992); Dhir, S. et al., "Regeneration of Fertile Plants from Protoplasts of Soybean (Glycine max L. Merr.): Genotypic Differences in Culture Response," Plant Cell Reports (1992) 11:285–289; Pandey, P. et al., "Plant Regeneration from Leaf and Hypocotyl Explants of Glycine wightii (W. and A.) VERDC. var longicauda," Japan J. Breed. 42:1–5 (1992); and Shetty, K., et al., "Stimulation of In Vitro Shoot Organogenesis in Glycine max (Merrill.) by Allantoin and Amides," Plant Science 81:(1992) 245–251; as well as U.S. Pat. No. 5,024,944, issued Jun. 18, 1991 to Collins et al. and U.S. Pat. No. 5,008,200, issued Apr. 16, 1991 to Ranch et al. Thus, another aspect of this invention is to provide cells that upon growth and differentiation produce soybean plants having all or essentially all the physiological and morphological characteristics of cultivar CL615261. The disclosures, publications, and patents that are disclosed herein are all hereby incorporated herein in their entirety by reference.

Industrial Applicability: The seed of soybean cultivar CL615261 further comprising one or more specific, single gene traits, the plant produced from the seed, the hybrid soybean plant produced from the crossing of the cultivar with any other soybean plant, hybrid seed, and various parts of the hybrid soybean plant can be utilized for human food, livestock feed, and as a raw material in industry.

Soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990.) Changes in fatty acid composition for improved oxidative stability and nutrition are constantly sought after. Industrial uses of soybean oil that is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils. Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein. For human consumption soybean meal is made into soybean flour that is processed to protein concentrates used for meat extenders or specialty pet foods. Production of edible protein ingredients from soybean offers a healthy, less expensive replacement for animal protein in meats as well as dairy-type products.

TABLE 1

Comparison between CL615261, Pioneer 91B33, Syngenta S15-B1, Pioneer 91B64, Asgrow AG1301 and Syngenta S14-M7 Data Summary 2002

| Cultivar | Yield | Maturity | Lodging | Height | Iron Chlorosis | Shatter |
|---|---|---|---|---|---|---|
| CL615261 | 49.7 | 118 | 2.8 | 72 | 2.5 | 4.1 |
| Pioneer 91B33 | 50.0 | 116 | 2.9 | 66 | 4.8 | 5.6 |
| Syngenta S15-B1 | 48.0 | 118 | 3.4 | 76 | 4.8 | 3.0 |
| Pioneer 91B64 | 47.1 | 119 | 3.1 | 73 | 6.0 | 5.0 |
| Asgrow AG1301 | 45.3 | 115 | 3.2 | 70 | 5.0 | 5.4 |
| Syngenta S14-M7 | 44.1 | 118 | 3.3 | 73 | 3.1 | 4.4 |
| LSD (0.5) | 2.7 | 1 | 0.6 | 9 | 1.6 | 2.5 |

Yield, bushels per acre; Maturity, date, 95% mature pod color; Lodging, 1=upright, 9=prostrate; Height, ground level to plant top; Sudden Death Syndrome, score, 1=no foliar symptoms, 9=severe symptoms; Shatter, score, 1=no seed shatter, 9=nearly complete shatter.

CL615261 is significantly higher yielding (LSD 0.05=2.7 bu/ac) than Syngenta Seeds cultivar S14-M7 and Asgrow AG 1301. CL615261 also has significantly better tolerance to Iron Deficiency Chlorosis (LSD0.05=1.6) than Pioneer 91 B64 and Asgrow AG1301.

DEPOSIT INFORMATION

Applicants have made a deposit of at least 2500 seeds of soybean cultivar CL615261 with the American Type Culture Collection (ATCC), Manassas, Va. 20110, ATCC Deposit No: PTA-6095. Access to this deposit will be available during the pendency of the application to the Commissioner of Patents and Trademarks and persons determined by the Commissioner to be entitled thereto upon request. Upon allowance of any claims in the application, the Applicants(s) will make the deposit available to the public pursuant to 37 CFR §1.808. Additionally, Applicants(s) will meet all the requirements of 37 C.F.R. §§1.801–1.809, including providing an indication of the viability of the sample when the deposit is made. This deposit of soybean cultivar CL615261 will be maintained in the ATCC Depository, which is a public depository, for a period of 30 years, or 5 years after the most recent request, or for the enforceable life of the patent, whichever is longer, and will be replaced if it ever becomes nonviable during that period. Applicants have no authority to waive any restrictions imposed by law on the transfer of biological material or its transportation in commerce. Applicants do not waive any infringement of its rights granted under this patent or under the Plant Variety Protection Act that may protect soybean cultivar CL615261.

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. Seed of soybean cultivar designated CL615261 representative seed of said soybean cultivar having been deposited under ATCC Accession No: PTA-6095.

2. A soybean plant, or a part thereof, produced by growing the seed of claim 1.

3. Pollen of the plant of claim 2.

4. An ovule of the plant of claim 2.

5. A soybean plant, or a part thereof, having all the physiological and morphological characteristics of the plant according to claim 2.

6. Seeds of the plant of claim 5, wherein plants produced by growing said seeds have all the physiological and morphological characteristics of the plants produced by growing seeds deposited under ATCC Accession No. PTA-6095.

7. A soybean plant produced from the soybean plant according to claim 2 by transformation with a transgene that confers upon said soybean plant tolerance to a herbicide.

8. The soybean plant according to claim 7, wherein said herbicide is glyphosate, glufosinate, a sulfonylurea or an imidazolinone herbicide, or a protoporphyrinogen oxidase inhibitor.

9. The soybean plant produced from the soybean plant according to claim 2 by transformation with a transgene that confers upon said soybean plant insect resistance, disease resistance, nematode resistance or virus resistance.

10. The soybean plant according to claim 9, wherein said transgene encodes VIP3.

11. The soybean plant produced from the soybean plant according to claim 2 by transformation with a transgene, wherein said transgene expresses thioredoxin and/or thioredoxin reductase.

12. A tissue culture of regenerable cells of the soybean plant according to claim 2.

13. The tissue culture according to claim 12, wherein the cells of said tissue culture are from a leaf, pollen, an embryo, a cotyledon, a hypocotyl, meristematic cells, a root, a root tip, an anther, a flower, a seed, a stem or a pod.

14. A soybean plant generated from the tissue culture of claim 12.

15. A soybean plant generated from the tissue culture of claim 12, wherein the regenerated plant is capable of expressing all of the morphological and physiological characteristics of soybean cultivar CL615261, representative seed of said soybean cultivar CL615261 having been deposited under ATCC Accesssion No. PTA-6095.

16. A method for producing a soybean seed comprising crossing a first parent soybean plant with a second parent soybean plant and harvesting the resultant first generation soybean seed, wherein said first or second parent soybean plant is a soybean plant according to claim 2 or a soybean plant having all the physiological and morphological characteristics of a plant according to claim 2.

17. A method for producing a CL615261-derived soybean plant, comprising:
   a) crossing inbred soybean line CL615261, representative seed of said soybean cultivar CL615261 having been deposited under ATCC Accession No. PTA-6095, with a second soybean plant to yield progeny soybean seed; and
   b) growing said progeny to yield said CL615261-derived soybean plant.

18. A tissue culture of regenerable cells of the soybean plant according to claim 5.

19. The tissue culture according to claim 18, wherein the cells of said tissue culture are from a leaf, pollen, an embryo, a cotyledon, a hypocotyl, meristematic cells, a root, a root tip, an anther, a flower, a seed, a stem or a pod.

20. A soybean plant generated from the tissue culture of claim 18.

21. A soybean plant generated from the tissue culture of claim 18, wherein the regenerated plant is capable of expressing all of the morphological and physiological characteristics of soybean cultivar CL615261, representative seed of said soybean cultivar CL615261 having been deposited under ATCC Accesssion No. PTA-6095.

* * * * *